(12) United States Patent
Fenchel

(10) Patent No.: US 9,763,638 B2
(45) Date of Patent: Sep. 19, 2017

(54) METHOD FOR CARRYING OUT A POSITRON EMISSION TOMOGRAPHY

(71) Applicant: Siemens Aktiengesellschaft, Munich (DE)

(72) Inventor: Matthias Fenchel, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 422 days.

(21) Appl. No.: 14/580,728

(22) Filed: Dec. 23, 2014

(65) Prior Publication Data

US 2015/0196266 A1    Jul. 16, 2015

(30) Foreign Application Priority Data

Jan. 10, 2014    (DE) .................. 10 2014 200 303

(51) Int. Cl.
*A61B 6/00*    (2006.01)
*A61B 6/03*    (2006.01)
(Continued)

(52) U.S. Cl.
CPC .......... *A61B 6/5247* (2013.01); *A61B 5/0035* (2013.01); *A61B 5/055* (2013.01); *A61B 5/7207* (2013.01); *A61B 6/037* (2013.01); *A61B 6/4417* (2013.01); *A61B 6/5205* (2013.01); *A61B 6/5258* (2013.01); *A61B 6/54* (2013.01); *G01R 33/481* (2013.01)

(58) Field of Classification Search
CPC ..... A61B 5/7207; A61B 5/0035; A61B 5/055; A61B 6/5247; A61B 6/037; A61B 6/5205; A61B 6/5258; A61B 6/4417; A61B 6/54; G01R 33/481

See application file for complete search history.

(56) References Cited

U.S. PATENT DOCUMENTS

2005/0129295 A1    6/2005   Bonner
2013/0320973 A1    12/2013  Bao

OTHER PUBLICATIONS

Mattias Hofmann, Bernd Pichler, Bernhard Schölkopf, Thomas Beyer: "Towards quantitative PET/MRI: a review of MR-based attenuation correction techniques", Eur. J. Nucl. Med. Mol. Imaging 36 (2009), pp. 93-104; Eur. J.; 2009.
(Continued)

*Primary Examiner* — Bo J Peng
(74) *Attorney, Agent, or Firm* — Harness, Dickey & Pierce, P.L.C.

(57) ABSTRACT

A method is disclosed for carrying out a positron emission tomography of an examination object in a hybrid system. In N consecutive time intervals, the following is carried out. For n=1 to n=N−1, nth magnetic resonance data and nth positron emission data is acquired in the nth time interval and as a function of this data, nth provisional attenuation correction values and nth provisional positron emission tomographies are determined during the (n+1)th time interval. In the Nth time interval Nth magnetic resonance data and Nth positron emission data is acquired and overall attenuation correction values are determined as a function of the Nth magnetic resonance data and the first to (N−1)th attenuation correction values and also a positron emission tomography is determined as a function of the overall attenuation correction values, the Nth positron emission data and the first to (N−1)th provisional positron emission tomographies.

20 Claims, 3 Drawing Sheets

(51) Int. Cl.
  *A61B 5/055* (2006.01)
  *A61B 5/00* (2006.01)
  *G01R 33/48* (2006.01)

(56) References Cited

OTHER PUBLICATIONS

H. Malcolm Hudson and Richard S. Larkin; "Accelerated Image Reconstruction Using Ordered Subsets of Projection Data"; IEEE Trans. on Medical Imaging, vol. 13, No. 4, Dec. 1994, pp. 601-609.
Johan Nuyts et al., "Completion of a Truncated Attenuation Image from the Attenuated PET Emission Data", IEEE Nuclear Science Symposium Conference Record, Knoxville, 2010.
German Office Action mailed Aug. 29, 2014.

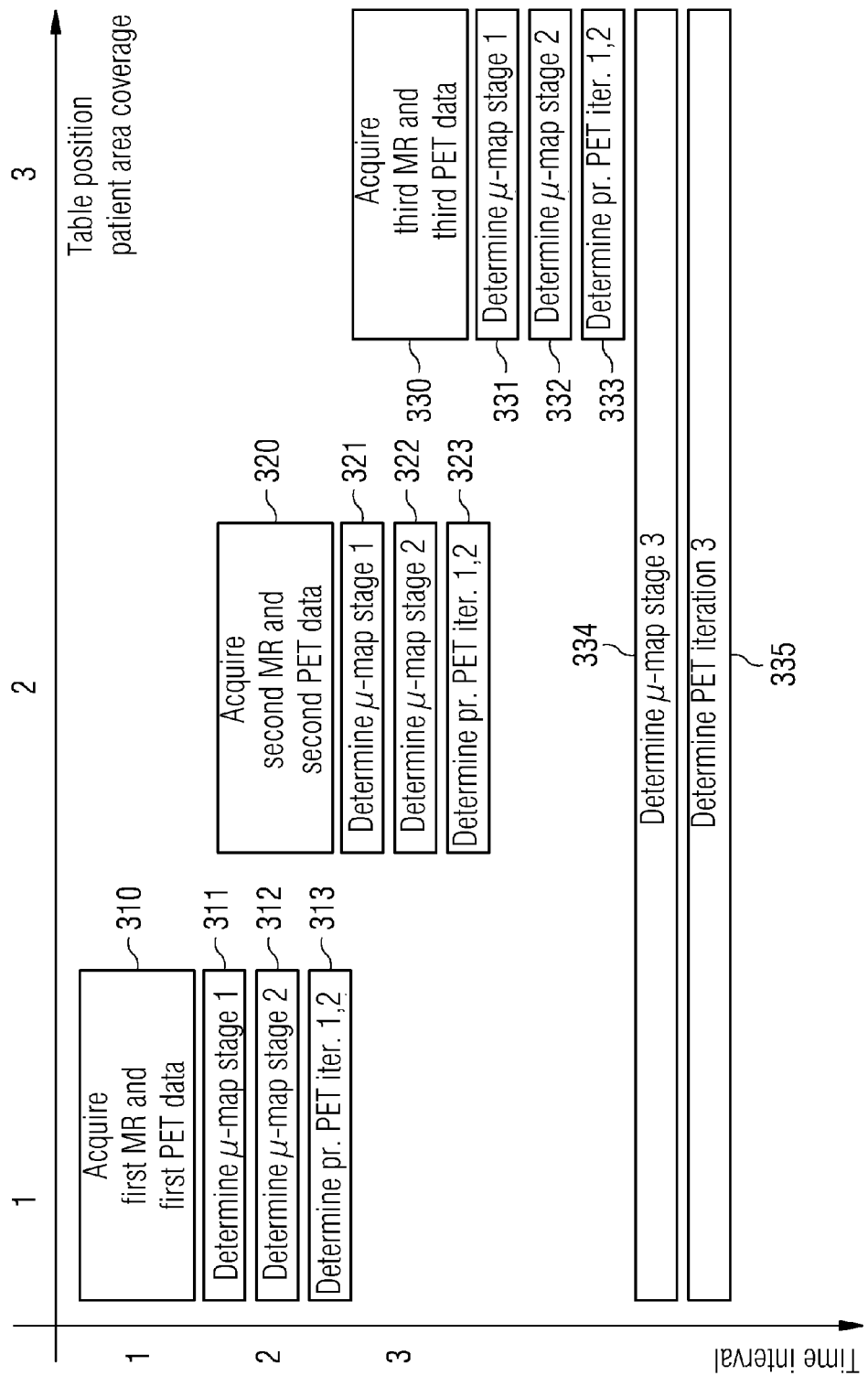

METHOD FOR CARRYING OUT A POSITRON EMISSION TOMOGRAPHY

PRIORITY STATEMENT

The present application hereby claims priority under 35 U.S.C. §119 to German patent application number DE 102014200303.2 filed Jan. 10, 2014, the entire contents of which are hereby incorporated herein by reference.

FIELD

At least one embodiment of the present invention generally relates to a method for carrying out a positron emission tomography, especially a combined magnetic resonance positron emission tomography, of an examination object in a hybrid system comprising a positron emission tomography system and a further tomography system, especially a magnetic resonance tomography system. At least one embodiment of the present invention further generally relates to a hybrid system for this purpose. At least one embodiment of the present invention generally relates to a method for performing combined magnetic resonance positron emission tomography in which magnetic resonance data and positron emission data is acquired at different table positions in turn and the data is processed at least partly temporally in parallel to the data acquisition.

BACKGROUND

Iterative reconstruction methods, such as e.g. AW-OSEM (Attenuation Weighted Ordered Subsets Expectation Maximization) or OP-OSEM (Ordinary Poisson Ordered Subsets Expectation Maximization), which are described in detail for example in the publication by Hudson, H. M., Larkin, R. S. (1994) "Accelerated image reconstruction using ordered subsets of projection data", IEEE Trans. Medical Imaging, 13 (4), 601-609, are used in the reconstruction of positron emission tomography images in conventional positron emission tomography systems (PET systems). These reconstruction algorithms compute images which, using a given Poisson noise model and a measured attenuation map (μ-map) exhibit a close match to the measured data.

On account of their iterative nature these algorithms are very time-intensive and their computation time rises in a linear manner with the number of iterations. In order to reduce the computation time at least partly, just an ordered number of subgroups of raw data groups, known as bins, can be used for each updating of the reconstructed image during the iterations. But even then the computation times are still so long that the reconstruction is aborted in typical clinical applications before the algorithms converge.

In combined magnetic resonance positron emission tomography systems (MR-PET) a human attenuation correction for the attenuation map for positron emission tomography based on magnetic resonance data is also determined. Therefore in MR-PET systems the reconstruction times are slowed down further by the fact that the attenuation correction is based on images and is usually performed on the basis of a combined image volume from a number of table stations, wherein a coverage of the Field of View (FoV) of the magnetic resonance system which is as large as possible is preferred in order to be able to use a largest possible anatomical context for model-based or model-supported segmentation algorithms of the lungs or the bones for example. An overview of magnetic resonance (MR)-based attenuation correction techniques can be found in the publication by Hofmann, M., B. Pichler, B. Schölkopf and T. Beyer: "Towards quantitative PET/MRI: a review of MR-based attenuation correction techniques" European Journal of Nuclear Medicine and Molecular Imaging 36(Supplement 1), 93-104 (03 2009). However, the consequence of using the largest possible FoV coverage is that a reconstruction of an MR-PET at different table stations, known as an MR-PET Multi-Station-Scan, can only be performed after the acquisition of the last table station, when a combination with a greatest possible coverage is fully available, while for example in a positron emission tomography/computed tomography (PET/CT) a computation for each table position can be performed immediately after the acquisition of the emission data has been concluded.

As previously described, magnetic-resonance-based attenuation correction is image-based and can furthermore exhibit different levels of complexity and precision in different stages. Each of these stages can depend on previous results and thus a sequential computation can be necessary. For example in a first step of the computation of the MR-based attenuation correction a simple foreground/background separation can be carried out, in a second step a lung segmentation can be performed within the foreground area, and a third step can consist of a segmentation of fatty and soft tissue within the foreground area. A next step can for example comprise a segmentation of a bone mask with the aid of orientation points and model-based image-processing technologies. In a further step objects outside the regular field of view can be added in, as is described for example in the publication by Johan Nuyts, Christian Michel, Matthias Fenchel, Girish Bal, Charles Watson. "Completion of a truncated attenuation image from the attenuated emission data". IEEE Nuclear Science Symposium Conference Record, Knoxville, 2010. A further step can comprise the computation or a so-called hardware attenuation correction map for each table station. This hardware attenuation correction map takes account of devices, such as e.g. local coils, which are disposed in the MR-PET system in the examination area. In a further step the computed segmented attenuation map can be refined locally in order for example to improve a consistency or freedom from contradictions, for example on the basis of a DCC (Discrete Consistency Condition) method or an MLAA (Maximum Likelihood of Attenuation and Activity) method, for example by the previously defined linear attenuation coefficients being adapted to more individual specific linear attenuation coefficients.

The steps given above need a significant time for the computation and can therefore delay the computation of the final PET image by a few minutes. The attenuation-corrected PET images are needed for a final quality check of the images before the patient can be released from the magnet resonance positron emission tomography system. The long computation times mean that a longer time is spent by the patient in the MR-PET system, which can be unpleasant for patients and additionally blocks the system for further patients.

Because of the fact that the attenuation correction in an MR-PET is image based and is based on a combined image, which preferably uses a largest possible field of view coverage, the attenuation-corrected PET reconstruction is only determined when the finished and complete attenuation correction map is available. In other words the attenuation-corrected PET reconstruction is delayed until such time as the finished attenuation correction map is available. FIG. 1 shows a schematic of a sequence of an attenuation-corrected PET reconstruction. First of all magnetic resonance and positron emission tomography data is acquired consecutively over time at three different table positions (steps 110-112) in order to acquire a desired coverage area of the patient. Seen in terms of time the attenuation correction maps are computed after the last acquisition 112 in different steps 113-115, which can at least partly depend on one another. Then, in step 116, the positron emission tomography images are reconstructed for example using an OSEM (Ordered Subsets Expectation Maximization) technology, which in its turn can require different iterations. Only after conclusion of the PET reconstruction can quality checks and evaluations of the positron emission tomography images take place and the patient be released from the MR-PET system.

In practice the computation of steps 113-116 can require five minutes for example for a usual examination with five table positions. These computation times can increase with more table positions and more attenuation correction algorithms.

The previously described time-intensive sequences during determination of the attenuation correction maps and the positron-emission tomography images cannot just occur in conjunction with a magnetic resonance positron emission tomography, but can also occur in other hybrid systems comprising a positron emission tomography system and a further tomography system. The further tomography system can be any given slice imaging modality, such as an ultrasound tomography system for example.

SUMMARY

At least one embodiment of the present invention is directed to accelerating the computation of positron emission tomography images in a positron emission tomography supported by a further tomography system.

In accordance with at least one embodiment of the present invention, a method is disclosed for carrying out a positron emission tomography of an examination object in a hybrid system, a hybrid system is disclosed, a computer program is disclosed and an electronically-readable data medium is disclosed. The dependent claims define preferred and advantageous forms of embodiment of the invention.

In accordance with at least one embodiment of the present invention, a method is disclosed for carrying out a positron emission tomography of an examination object in a hybrid system is provided. The hybrid system comprises a positron emission tomography system and a further tomography system or slice-imaging modality, especially a magnetic resonance tomography system.

At least one embodiment of the present invention therefore especially relates to a method for performing a combined magnetic resonance positron emission tomography (MR-PET) of the examination object in a magnetic resonance positron emission tomography system. In N consecutive time intervals tomography data is acquired in each case via the further tomography system and positron emission data of the examination object is acquired. The N consecutive time intervals can for example be times at which an examination table remains at a corresponding examination table position, while the examination object, for example a patient, is located on the examination table and is moved from one table position to the next table position. In other words a patient can be disposed for example in a specific number N of examination table positions relative to the hybrid system and at each of these table positions tomography data and positron emission data of the patient is acquired. A typical number of table positions N can range between three and ten or more.

For performing the method in a magnetic resonance positron emission tomography system corresponding magnetic resonance data is acquired as tomography data by way of the magnetic resonance system. The method comprises iteratively performing the following steps (a)-(c) for the first N−1 time intervals or table positions. In the description of the performance of the method steps (a)-(c) a run variable n is used, which accordingly runs from n=1 to n=N−1. In step (a) nth tomography data and nth positron emission data is acquired for the nth time interval. In step (b), depending on the data acquired in step (a), attenuation correction values are determined for a positron emission tomography, and this is done during the (n+1)th time interval, i.e. while the next magnetic resonance data and positron emission data is being acquired for the next table position. In other words in step (b) nth attenuation correction values for a positron emission tomography are determined as a function of the nth tomography data during the (n+1)th time interval. The determination of the nth attenuation correction values in the (n+1)th time interval also means in this context that the nth attenuation correction values can as an alternative or in addition be determined in the (n+2)th, (n+3)th or another later time interval, provided further tomography data and positron emission data is acquired in this later time interval. In step (c), depending on the positron emission data acquired in step (a) and the attenuation correction values determined in step (b), provisional positron emission tomographies are already determined, wherein this determination is likewise performed if the examination table is already located in the next position or in yet another table position. In other words in step (c) an nth provisional positron emission tomography is determined as a function of the nth positron emission data and the nth attenuation correction values during the (n+1)th time interval.

The steps (a)-(c) are performed for each time interval 1 to N−1, wherein in each case during the acquisition of tomography data and positron emission data in a time interval, the tomography data and the positron emission data which was acquired in the preceding time interval is evaluated. Since however at this point in time no complete tomography data over the entire field of view is present in each case, initially only attenuation correction values can be determined for example, which can be determined independently of the overall anatomical characteristics of the examination object. In other words, for determining the nth attenuation correction values of the steps (a)-(c), information from the tomography data is used which can already be determined locally for a specific table position.

In accordance with at least one embodiment of the present invention, a hybrid system is also provided which comprises a positron emission tomography system and a further tomography system, especially a magnetic resonance tomography system. The hybrid system can therefore for example comprise a magnetic resonance positron emission tomography system, which comprises a basic field magnet, a gradient field system, a radio-frequency antenna and a control device for activating the gradient field system and the radio frequency antenna for receiving measurement signals picked up by the radio-frequency antenna, for evaluating the measurement signals and for creating magnetic resonance tomography images. The hybrid system further includes detectors for acquisition of photons which have been created by an annihilation of electrons and positrons in an examination object, as well as a control device for evaluation of signals of the detectors and for creating positron emission tomography images.

The hybrid system is capable, in N consecutive time intervals, of acquiring in each case tomography data acquired via the further tomography system and positron emission data is acquired via the positron emission tomography system. In this case the system is designed, for the time intervals from n=1 to n=N−1 in each case (a) to acquire nth tomography data and nth positron emission data in the nth time interval, (b) to determine nth attenuation correction values for a positron emission tomography depending on the nth tomography data during the (n+1)th interval and (c) to determine an nth provisional positron emission tomography depending on the nth positron emission data and the nth attenuation correction values during the (n+1)th time interval.

Furthermore in accordance with at least one embodiment of the present invention, a computer program is provided which can be loaded into a memory of a programmable controller of a hybrid system. With this computer program, all or various of the previously described forms of embodiment of the inventive method can be carried out when the computer program is running in the controller.

In this case the computer program may possibly need program segments or program modules, i.e. libraries or auxiliary functions, in order to realize the corresponding forms of embodiment. In other words a computer program or software is particularly to be protected with the claim directed to the computer program with which one of the above described forms of embodiment of the inventive method can be carried out or which carries out this form of embodiment. In this case, the software can involve a source code, e.g. C++, which still has to be compiled or translated and linked or which only has to be interpreted or can involve an executable software code which only has to be loaded into the corresponding controller for execution.

Finally, at least one embodiment of the present invention provides an electronically-readable data medium, for example a DVD, a magnetic tape or a USB stick on which electronically readable control information, especially software as described above, is stored. When this control information is read from the data medium and is stored in a controller, all inventive forms of embodiment of the described method can be carried out.

BRIEF DESCRIPTION OF THE DRAWINGS

The present invention will be explained below with reference to the drawings on the basis of preferred forms of embodiment.

FIG. 3 shows a schematic of a method for carrying out a combined magnetic resonance positron emission tomography in accordance with a form of embodiment of the present invention.

DETAILED DESCRIPTION OF THE EXAMPLE EMBODIMENTS

Figure 1:
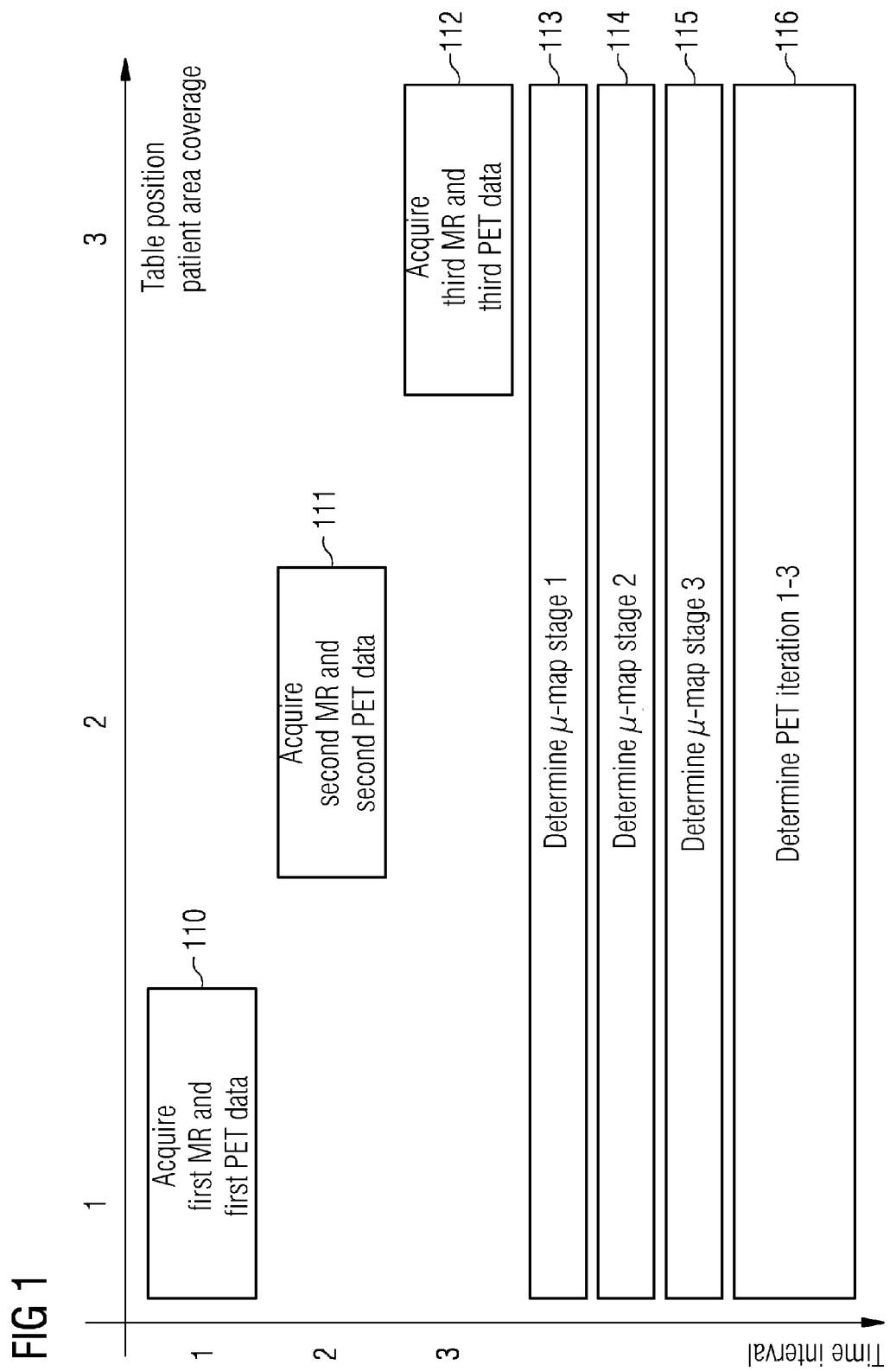
FIG. 1 shows a method for carrying out a combined magnetic resonance positron emission tomography of an examination object in a magnetic resonance positron emission tomography system in accordance with the prior art.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the present invention, a method is disclosed for carrying out a positron emission tomography of an examination object in a hybrid system is provided. The hybrid system comprises a positron emission tomography system and a further tomography system or slice-imaging modality, especially a magnetic resonance tomography system.

At least one embodiment of the present invention therefore especially relates to a method for performing a combined magnetic resonance positron emission tomography (MR-PET) of the examination object in a magnetic resonance positron emission tomography system. In N consecutive time intervals tomography data is acquired in each case via the further tomography system and positron emission data of the examination object is acquired. The N consecutive time intervals can for example be times at which an examination table remains at a corresponding examination table position, while the examination object, for example a patient, is located on the examination table and is moved from one table position to the next table position. In other words a patient can be disposed for example in a specific number N of examination table positions relative to the hybrid system and at each of these table positions tomography data and positron emission data of the patient is acquired. A typical number of table positions N can range between three and ten or more.

For performing the method in a magnetic resonance positron emission tomography system corresponding magnetic resonance data is acquired as tomography data by way of the magnetic resonance system. The method comprises iteratively performing the following steps (a)-(c) for the first N−1 time intervals or table positions. In the description of the performance of the method steps (a)-(c) a run variable n is used, which accordingly runs from n=1 to n=N−1. In step (a) nth tomography data and nth positron emission data is acquired for the nth time interval. In step (b), depending on the data acquired in step (a), attenuation correction values are determined for a positron emission tomography, and this is done during the (n+1)th time interval, i.e. while the next magnetic resonance data and positron emission data is being acquired for the next table position. In other words in step (b) nth attenuation correction values for a positron emission tomography are determined as a function of the nth tomography data during the (n+1)th time interval. The determination of the nth attenuation correction values in the (n+1)th time interval also means in this context that the nth attenuation correction values can as an alternative or in addition be determined in the (n+2)th, (n+3)th or another later time interval, provided further tomography data and positron emission data is acquired in this later time interval. In step (c), depending on the positron emission data acquired in step (a) and the attenuation correction values determined in step (b), provisional positron emission tomographies are already determined, wherein this determination is likewise performed if the examination table is already located in the next position or in yet another table position. In other words in step (c) an nth provisional positron emission tomography is determined as a function of the nth positron emission data and the nth attenuation correction values during the (n+1)th time interval.

The steps (a)-(c) are performed for each time interval 1 to N−1, wherein in each case during the acquisition of tomography data and positron emission data in a time interval, the tomography data and the positron emission data which was acquired in the preceding time interval is evaluated. Since however at this point in time no complete tomography data over the entire field of view is present in each case, initially only attenuation correction values can be determined for example, which can be determined independently of the overall anatomical characteristics of the examination object. In other words, for determining the nth attenuation correction values of the steps (a)-(c), information from the tomography data is used which can already be determined locally for a specific table position.

For example, the determination of the nth attenuation correction values can therefore comprise assigning respective foreground/background information to pixels determined from the tomography data. The respective foreground/background information specifies whether the respective pixel is assigned to an area of the examination object or not.

As an alternative or in addition, determining the nth attenuation correction values of the steps (a)-(c) can comprise assigning respective fatty/soft tissue information to pixels determined from the tomography data. The respective fatty/soft tissue information specifies whether the respective pixel is assigned to a soft tissue area of the examination object (for example with a predominant proportion of water) or is assigned to an area of the examination object with a predominant proportion of fat. This information is usually able to be determined from the magnetic resonance data which is acquired locally at a table position for example and is therefore available already at the end of an acquisition of magnetic resonance data of a table position.

Furthermore the determination of the nth attenuation correction values can comprise an assignment of respective device information to pixels determined from the tomography data. The respective device information specifies whether the respective pixel is assigned to an area of an additional device disposed in the examination area of the hybrid system. Such an additional device can for example include a local coil which is disposed on or at a patient, if the further tomography system comprises a magnetic resonance tomography system for example. This information is already able to be determined from magnetic resonance data, or metadata, which describes the coil configurations/hardware configurations which are detected locally at a table position.

With the aid of the information given above an attenuation correction map can be determined from the tomography data, which although it does not yet include overall anatomical data, is however already sufficiently accurate to determine the at least one provisional positron emission tomography. If the steps (a)-(c) have been performed for n=1 to n=N−1, in the Nth time interval, i.e. in the last time interval or at the last planned examination table position, Nth tomography data and Nth positron emission data is acquired and on the basis of this data and the attenuation corrections and preliminary positron emission tomographies determined in steps (a)-(c) for the preceding table positions or time intervals, final attenuation correction values and a final positron emission tomography are finally determined. The fact that at least provisional attenuation correction maps and positron emission tomography images are already created during the acquisition of the tomography data and the positron emission data at the different table positions enables the computing overhead for determining the final positron emission tomography images after the acquisition of the tomography data and positron emission data at the last table position to be significantly reduced, so that an assessment of the quality of the acquired data after acquisition at the last table position is possible earlier and therefore the patient can also be released from the system earlier. This enables the time that the patient spends in the system to be reduced and the throughput of patients at the system to be increased.

In accordance with one form of embodiment the overall final attenuation correction values are determined as a function of anatomical characteristics of the examination object. For example the pixels of a magnetic resonance image determined from the magnetic resonance data can be assigned lung information in each case, which specifies for each pixel whether the respective pixel is assigned to an area of the lungs of the examination object or not. As an alternative or in addition respective bone information can be assigned to a pixel of a magnetic resonance image, which specifies for each pixel whether the respective pixel is assigned to an area of a bone of the examination object or not. Such anatomical characteristics can be assigned with the aid of orientation points, known as landmarks, or with the aid of models. By taking into account the anatomical characteristics of the examination object, attenuation correction values can be determined with high accuracy and thus a very accurate attenuation correction map can be determined.

In a further form of embodiment the nth attenuation correction values, which are determined for a respective table position while the above steps (a)-(c) are being performed, are determined based on predetermined discrete consistency conditions which are based on local information and thus contribute to detecting and correcting local conflicts. Usual technologies such as e.g. DCC (Discrete Consistency Conditions) or MLAA (Maximum Likelihood of Attenuation and Activity) can be used for this purpose. The attenuation correction values thus determined already provide sufficient accuracy for reconstructing at least provisional positron emission tomography images, i.e. creating attenuation-corrected PET images for each table position. The provisional PET images are stored until an attenuation map with a next level of accuracy is available. This leads to a plurality of computing steps, but each of the steps converges more quickly, since only a smaller difference from the previous state exists.

In a further form of embodiment, the determination of the provisional positron emission tomographies and also the determination of the final positron emission tomography comprises in each case a determination of coincidence events which have been caused by scattered photons. The coincidence events can be determined as a function of the available attenuation correction values. In this way scattering influences, known as "scatter", can already be determined on the basis of rough attenuation correction maps which are determined in the steps (a)-(c) for the different table positions, and are refined iteratively with the availability of more detailed and more accurate steps of the attenuation correction maps. This enables a large part of the computation of the scatter to be performed already during the acquisition of the magnetic resonance data and positron emission data, so that computations according to the last table position can be shortened accordingly.

In a further form of embodiment, a provisional positron emission tomography is determined by an iterative back projection method using an expectation maximization algorithm for object subsets. The expectation maximization algorithm for object subsets is executed as a function of the positron emission data which was acquired at the corresponding table position. Expectation maximization algorithms for object subsets are known by the term "Ordered Subsets Expectation Maximization" (OS-EM) and can be determined for creation of at least provisional positron emission tomographies on the basis of local positron emission data which has been corrected with the aid of local attenuation correction values.

Thus many steps of the back projection method can already be performed while further tomography data and positron emission data is detected at subsequent table positions. After the acquisition of the tomography data and positron emission data at the last table position the iterative back projection method can be determined using the OS-EM algorithm, taking into account the positron emission data for the last table position and the results of the previously determined provisional positron emission tomographies. By using the provisional positron emission tomographies the final positron emission tomography can converge more rapidly and thus be determined in a shorter time.

In accordance with at least one embodiment of the present invention, a hybrid system is also provided which comprises a positron emission tomography system and a further tomography system, especially a magnetic resonance tomography system. The hybrid system can therefore for example comprise a magnetic resonance positron emission tomography system, which comprises a basic field magnet, a gradient field system, a radio-frequency antenna and a control device for activating the gradient field system and the radio frequency antenna for receiving measurement signals picked up by the radio-frequency antenna, for evaluating the measurement signals and for creating magnetic resonance tomography images. The hybrid system further includes detectors for acquisition of photons which have been created by an annihilation of electrons and positrons in an examination object, as well as a control device for evaluation of signals of the detectors and for creating positron emission tomography images.

The hybrid system is capable, in N consecutive time intervals, of acquiring in each case tomography data acquired via the further tomography system and positron emission data is acquired via the positron emission tomography system. In this case the system is designed, for the time intervals from n=1 to n=N−1 in each case (d) to acquire nth tomography data and nth positron emission data in the nth time interval, (e) to determine nth attenuation correction values for a positron emission tomography depending on the nth tomography data during the (n+1)th interval and (f) to determine an nth provisional positron emission tomography depending on the nth positron emission data and the nth attenuation correction values during the (n+1)th time interval.

The hybrid system is further capable, in the last time interval i.e. in the Nth time interval, of acquiring corresponding Nth tomography data and nth positron emission data and depending on the Nth tomography data and the first to (N−1)th attenuation correction values, of determining the overall attenuation correction values for a positron emission tomography and depending on the overall attenuation correction values, of determining for the Nth positron emission data and the first to (N−1)th provisional positron emission tomographies an overall positron emission tomography. The hybrid system is therefore suitable for carrying out the previously described method and its forms of embodiment and therefore also includes the advantages previously described in conjunction with the method.

Furthermore in accordance with at least one embodiment of the present invention, a computer program is provided which can be loaded into a memory of a programmable controller of a hybrid system. With this computer program, all or various of the previously described forms of embodiment of the inventive method can be carried out when the computer program is running in the controller.

In this case the computer program may possibly need program segments or program modules, i.e. libraries or auxiliary functions, in order to realize the corresponding forms of embodiment. In other words a computer program or software is particularly to be protected with the claim directed to the computer program with which one of the above described forms of embodiment of the inventive method can be carried out or which carries out this form of embodiment. In this case, the software can involve a source code, e.g. C++, which still has to be compiled or translated and linked or which only has to be interpreted or can involve an executable software code which only has to be loaded into the corresponding controller for execution.

Finally, at least one embodiment of the present invention provides an electronically-readable data medium, for example a DVD, a magnetic tape or a USB stick on which electronically readable control information, especially software as described above, is stored. When this control information is read from the data medium and is stored in a controller, all inventive forms of embodiment of the described method can be carried out.

Figure 2:
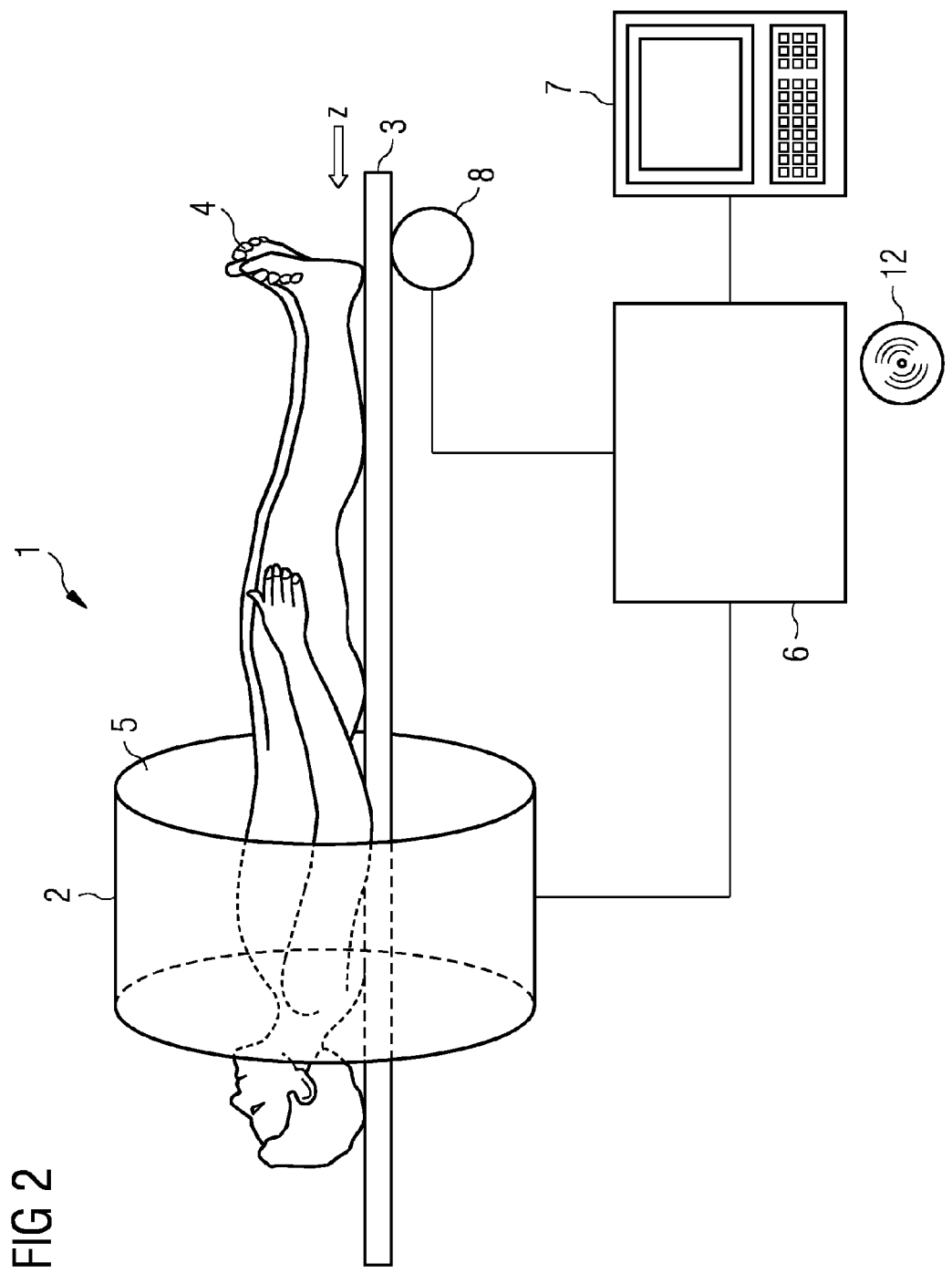
FIG. 2 shows a schematic of a magnetic resonance positron emission tomography system in accordance with a form of embodiment of the present invention.

FIG. 2 shows a schematic diagram of a magnetic resonance positron emission tomography system 1. The system 1 comprises a tomograph 2, an examination table 3 for a patient 4 who can be moved on the examination table 3 through an opening 5 of the tomograph, a control device 6, an evaluation facility 7 and a drive unit 8. The control device 6 activates the tomograph 2 and receives from the tomograph 2 signals which are picked up by the tomograph 2. With the aid of the tomograph 2 both magnetic resonance data and also positron emission data can be provided. To create the magnetic resonance data the tomograph 2 has a basic field magnet not shown in the diagram, which creates a basic magnetic field B0, and also a gradient field system not shown in the diagram for creating gradient fields. Furthermore the tomograph 2 includes one or more radio frequency antennas for creating radio-frequency signals and for receiving measurement signals which are used by the control device 6 and the evaluation facility 7 for creating magnetic resonance images. Also disposed in the tomograph 2 are detectors for acquiring photons which are created by annihilation of electrons and positrons in the examination object 4. The control device 6 is further designed for receiving signals from the detectors and is capable of evaluating these signals for creating positron emission tomography images. The control device 6 further activates the drive unit 8 in order to move the examination table 3 in a direction Z together with the patient 4 through the opening 5 of the tomograph 2. The control device 6 and the evaluation facility 7 can for example comprise a computer system with a screen, a keyboard and a data medium 12 on which electronically-readable control information is stored, which is embodied so that it carries out the method described below when the data medium 12 is used in the evaluation facility 7 and the control device 6.

Instead of, as has been shown in conjunction with FIG. 1, first acquiring magnetic resonance data and positron emission data at different table positions in steps 110-112 and then subsequently making a complete attenuation correction map and carrying out the PET reconstruction on the basis of the complete attenuation correction map (steps 113-116), the method described below in conjunction with FIG. 3 is carried out.

FIG. 3 shows a schematic of the sequence of a method, wherein a spatial coverage of the information established in relation to the patient at different table positions is shown in the x-axis and a temporal graph of the times at which information was acquired and computed is shown on the y-axis. In step 301 the patient 4 together with the examination table 3 is located at a first table position. At this first table position first magnetic resonance data and positron emission data is acquired. After the acquisition of the magnetic resonance data and positron emission data at the first table position has been concluded, the table is moved to a second position. There, in step 302, second magnetic resonance data and positron emission data is acquired for the second table position. At the same time, on the basis of the first magnetic resonance data acquired at the first table position, attenuation correction values for a positron emission tomography are computed. The attenuation correction values can be entered into an attenuation correction map, known as a μ-map. For example in a step 311 a background/foreground separation and/or a fatty and soft tissue segmentation can be carried out in the foreground. In step 312 the attenuation correction values can be refined for example by consistency checks carried out locally, for example on the basis of a DCC (Discrete Consistency Condition) or MLAA (Maximum Likelihood of Attenuation and Activity), by for example the predefined linear attenuation coefficients being modified to more individual specific linear attenuation coefficients.

Furthermore, in step 312, hardware components can be taken into consideration which were disposed in the tomograph 2 during the acquisition of the first magnetic resonance data and positron emission data at the first table position, for example local coils. Corresponding attenuation correction values for these hardware components can be determined in step 312.

On the basis of the attenuation correction values thus determined, in step 313 provisional positron emission tomography is determined using the positron emission data acquired in step 310 at the first table position. The step 313 is also carried out while the table is already disposed at the second position and the second magnetic resonance data and positron emission data is being acquired at the second position in step 320. For determining the provisional positron emission tomography, in step 313 for example an algorithm for expectation maximization for object subsets can be used which is known by the term OSEM (Ordered Subsets Expectation Maximization). Other methods for evaluation of the positron emission data using the attenuation correction values can however likewise be used.

After the second magnetic resonance data and positron emission data has been determined at the second table position in step 320, the examination table 3 together with the patient 4 is moved into a further position 3 and there, in step 330, third magnetic resonance data and positron emission data is acquired. During this acquisition of the third magnetic resonance data and positron emission data, attenuation correction values and provisional positron emission tomographies are again determined in steps 321, 322 and 323 on the basis of the second magnetic resonance data and positron emission data acquired at the second table position. After the third magnetic resonance data and positron emission data has been acquired at the third table position in step 330, in steps 331, 332 and 333 corresponding attenuation correction values and provisional positron emission tomographies are determined for the third table position. Subsequently, in step 334 attenuation correction values are determined for the entire examination area which includes all three table positions. In this case for example anatomy-dependent information, such as e.g. a lung segmentation or a bone segmentation, can be used in order to create more precise attenuation correction values and thus a more precise attenuation correction map. In this case the attenuation correction values which were determined in steps 311, 312, 321, 322 and 331, 332 are used, through which the determination of the final attenuation correction map in step 334 requires significantly lower computing outlay than the determination of the attenuation correction map in the steps 113-115 in accordance with the prior art.

On the basis of the attenuation correction map created in step 334, in step 335 a final positron emission tomography is determined, wherein once again the provisional positron emission tomographies of the steps 313, 323 and 333 are used so that for example the OSEM algorithm converges more quickly, through which the positron emission tomography images can be determined more quickly than is possible for example in the prior art in step 116.

In the example described above the magnetic resonance data and positron emission data was determined at three different table positions in turn. The present method is however not restricted to three table positions but can be expanded to any given number of table positions. The decisive factor here is that the evaluation of the magnetic resonance data and positron emission data from one table position already begins when the table is moved to the next position and further magnetic resonance data and positron emission data is acquired there. Therefore provisional attenuation-corrected PET images are computed after each table position. These intermediate PET images are stored until subsequent more accurate attenuation correction maps are available. This leads to a plurality of computation steps, but each of the steps can converge significantly more quickly, since in each case there is only a smaller difference from the preceding state. In addition these steps can be carried out in parallel to the computation of the attenuation correction map, so that overall an increase in performance can be achieved.

The method described above can further be expanded such that what is known as a "scatter simulation" is iteratively calculated. Scatter relates to coincidence events which are caused by scattered photons. This scatter can initially be computed on the basis of rough provisional attenuation correction values and can be refined when more detailed and more accurate attenuation correction values are available.

In summary the PET-OSEM reconstruction and the scatter simulation are nested with the computation of the attenuation correction map at the different acquisition times of the different table positions. Through this attenuation-corrected PET images with gradually increasing accuracy are rapidly available. This makes possible rapid quality checking and rapid acquisition and provision of the positron emission tomographies.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for performing a positron emission tomography of an examination object in a hybrid system which includes a positron emission tomography system and a further tomography system, wherein in N consecutive time intervals tomography data is acquired via the further tomography system time and positron emission data of the examination object is acquired in each case, the method comprising:

carrying out (a) to (c) for n=1 to n=N−1,
  (a) acquiring nth tomography data and nth positron emission data in the nth time interval,
  (b) determining nth attenuation correction values for a positron emission tomography as a function of the nth tomography data during the (n+1)th time interval, and
  (c) determining an nth provisional positron emission tomography as a function of the nth positron emission data and the nth attenuation correction values during the (n+1)th time interval;

aquiring Nth tomography data and Nth positron emission data in the Nth time interval;

determining the overall attenuation correction values for a positron emission tomography as a function of the Nth tomography data and the first to (N−1)th attenuation correction values; and determining a positron emission tomography as a function of the overall attenuation correction values, the Nth positron emission data and the first to (N−1)th provisional positron emission tomographies.

2. The method of claim 1, wherein the hybrid system includes a magnetic resonance positron emission tomography system, the magnetic resonance positron emission tomography system including the positron emission tomography system and a magnetic resonance tomography system as the further tomography system, and wherein the tomography data comprises magnetic resonance data.

3. The method of claim 2, wherein the determination of the nth attenuation correction values includes a determination of the nth attenuation correction values independently of anatomical characteristics of the examination object.

4. The method of claim 1, wherein the determination of the nth attenuation correction values includes a determination of the nth attenuation correction values independently of anatomical characteristics of the examination object.

5. The method of claim 1, wherein the determination of the nth attenuation correction values comprises at least one of:

assigning respective foreground/background information to the pixels determined from the tomography data, wherein the respective foreground/background information specifies whether the respective pixel is assigned to an area of the examination object;

assigning respective fat/water information to pixels determined from the tomography data, wherein the respective fat/water information specifies whether the respective pixel is assigned to an area of the examination object with a predominant proportion of water or to an area of the examination object with a predominant proportion of fat; and assigning respective device information to pixels determined from the tomography data, wherein the respective device information specifies whether the respective pixel is assigned to an area of an additional device disposed in the examination area of the hybrid system.

6. The method of claim 5, wherein the determination of the nth attenuation correction values comprises:

determining an attenuation map for the provisional positron emission tomography as a function of the information assigned to the pixels.

7. The method of claim 1, wherein the determination of the overall attenuation correction values includes a determination of the overall attenuation correction values as a function of anatomical characteristics of the examination object.

8. The method of claim 1, wherein the determination of the overall attenuation correction values includes at least one of:

assigning respective lung information to pixels determined from the tomography data, wherein the respective lung information specifies whether the respective pixel is assigned to an area of the lungs of the examination object; and assigning respective bone information to pixels determined from the tomography data, wherein the respective bone information specifies whether the respective pixel is assigned to an area of the bone of the examination object.

9. The method of claim 8, wherein the determination of the overall attenuation correction values comprises:

determining an overall attenuation correction map for the positron emission tomography as a function of the information assigned to the pixels.

10. The method of claim 1, wherein the determination of the nth attenuation correction values includes at least one of:

determining the nth attenuation correction values based on predetermined discrete consistency conditions; and determining the nth attenuation correction values with the aid of a reconstruction based on a predetermined maximum expectation for the attenuation and activity.

11. The method of claim 1, wherein the determination of the nth provisional positron emission tomography includes:

determining nth coincidence events caused by scattered photons as a function of the nth attenuation correction values.

12. The method of claim 11, wherein the determination of the positron emission tomography comprises:

determining Nth coincidence events caused by scattered photons as a function of the Nth attenuation correction values and the first to (N−1)th coincidence events.

13. The method of claim 1, wherein the determination of the nth provisional positron emission tomography includes:

carrying out an iterative back projection method using an expectation maximization algorithm for object subsets as a function of the nth positron emission data.

14. The method of claim 13, wherein the determination of the positron emission tomography includes:

carrying out an iterative back projection method using an expectation maximization algorithm for object subsets as a function of the Nth positron emission data and results of the use of the expectation maximization algorithm for object subsets as a function of the nth positron emission data.

15. The method of claim 1, wherein the examination object is disposed in different positions in relation to the hybrid system, wherein each position is assigned to one of the N time intervals.

16. A hybrid system, comprising:

a positron emission tomography system;

a further tomography system;

a computer system to evaluate measurement signals from the further tomography system and to create tomography images;

detectors to acquire photons, created by annihilation of electrons and positrons in an examination object; and a computer system to evaluate signals of the detectors and to create positron emission tomography images, wherein the hybrid system is embodied, in N consecutive time intervals, to acquire tomography data and positron emission data of the examination object in each case, wherein the hybrid system is embodied, for the time intervals n=1 to n=N−1 in each case (a) to acquire nth tomography data and nth positron emission data in the nth time interval, (b) to determine nth attenuation correction values for a positron emission tomography as a function of the nth tomography data during the (n+1)th time interval, and (c) to determine an nth provisional positron emission tomography as a function of the nth positron emission data and the nth attenuation correction values during the (n+1)th time interval, wherein the hybrid system is further embodied, to acquire Nth tomography data and Nth positron emission data in the Nth time interval, to determine the overall attenuation correction values for a positron emission tomography as a function of the Nth tomography data and the first to (N−1)th attenuation correction values, and to determine an emission tomography as a function of the overall attenuation correction values, the Nth positron emission data and the first to (N−1)th provisional positron emission tomographies.

17. The hybrid system of claim 16, wherein the hybrid system includes a magnetic resonance positron emission tomography system, the magnetic resonance positron emission tomography system including the positron emission tomography system and a magnetic resonance tomography system as the further tomography system, and wherein the tomography data comprises magnetic resonance data.

18. A non-transitory memory including computer program including program segments for carrying out the method of claim 1 when the program is executed in a computer system of a hybrid system.

19. A non-transitory electronically-readable data medium including electronically-readable control information stored thereon, embodied so as to execute the method of claim 1 when the data medium is used in a computer system of a hybrid system.

20. A non-transitory electronically-readable data medium including electronically-readable control information stored thereon, embodied so as to execute the method of claim 2 when the data medium is used in a computer system of a hybrid system.

* * * * *